(12) United States Patent
Räther et al.

(10) Patent No.: US 8,080,787 B2
(45) Date of Patent: Dec. 20, 2011

(54) ION MOBILITY MEASUREMENT AT A POTENTIAL BARRIER

(75) Inventors: Oliver Räther, Bremen (DE); Gökhan Baykut, Bremen (DE); Jochen Franzen, Bremen (DE)

(73) Assignee: Bruker Daltonik GmbH, Bremen (DE)

( * ) Notice: Subject to any disclaimer, the term of this patent is extended or adjusted under 35 U.S.C. 154(b) by 275 days.

(21) Appl. No.: 12/548,945

(22) Filed: Aug. 27, 2009

(65) Prior Publication Data

US 2010/0090102 A1    Apr. 15, 2010

(30) Foreign Application Priority Data

Sep. 4, 2008  (DE) .......................... 10 2008 045 941
Oct. 15, 2008 (DE) .......................... 10 2008 051 695

(51) Int. Cl.
*B01D 59/44* (2006.01)
(52) U.S. Cl. .................... 250/290; 250/282; 250/288
(58) Field of Classification Search .................. 250/290
See application file for complete search history.

(56) References Cited

U.S. PATENT DOCUMENTS

| | | | |
|---|---|---|---|
| 7,385,187 B2 * | 6/2008 | Verentchikov et al. | 250/287 |
| 2006/0151692 A1 * | 7/2006 | Collings et al. | 250/290 |
| 2007/0034810 A1 | 2/2007 | Hoyes | |
| 2009/0194687 A1 * | 8/2009 | Jolliffe et al. | 250/288 |

FOREIGN PATENT DOCUMENTS

| | | |
|---|---|---|
| GB | 2 409 764 B | 5/2006 |
| GB | 2 457 708 A | 8/2009 |
| WO | WO 2004/109741 A2 | 12/2004 |
| WO | WO 2007/010272 A2 | 1/2007 |
| WO | WO 2007/054712 A2 | 5/2007 |

OTHER PUBLICATIONS

Page, et al., "Variable Low-Mass Filtering Using an Electrodynamic Ion Funnel," Journal of Mass Spectrometry, vol. 40, pp. 1215-1222, 2005.

* cited by examiner

*Primary Examiner* — Phillip A Johnston
(74) *Attorney, Agent, or Firm* — Law Offices of Paul E. Kudirka

(57) ABSTRACT

Ion mobilities are measured by entraining the ions in a gas and adiabatically expanding the ion-containing gas through a nozzle to form a gas jet. An electrical field barrier with variable height is located at the nozzle exit. The field barrier may be located adjacent to the nozzle exit or an ion guide may be located between the nozzle and the field barrier. If a continuous ion current is supplied, the height of the barrier is varied and the ion current of the ions passing over the barrier is measured, the ion current can be differentiated to generate a mobility spectrum. Alternatively, the ions can be temporarily stored in the ion guide so that measurement of the ion current of the ions passing over the barrier results in a direct measurement of the mobility spectrum.

21 Claims, 4 Drawing Sheets

ION MOBILITY MEASUREMENT AT A POTENTIAL BARRIER

BACKGROUND

The invention relates to measurements of ion mobilities in gases under the influence of electric fields. Mass spectrometers can only ever determine the ratio of the ion mass to the charge of the ion. In the following, the term "mass of an ion" or "ion mass", which is used for the sake of simplicity, always refers to the ratio of the mass m to the number of elementary charges z of the ion. This charge-related mass m/z has the physical dimension of a mass; it is often called "mass-to-charge ratio", although this is dimensionally incorrect. "Ion species" shall denote those ions having the same elementary composition, the same charge and the same structure. The ion species generally comprises all the ions of an isotope group, which may well include ions of slightly different masses, but virtually the same mobilities.

Isomers of the primary structure of bioorganic molecules (structural isomers) and isomers of the secondary or tertiary structure (conformational isomers) show different geometrical forms but exactly the same mass. It is therefore impossible to differentiate between them on the basis of their mass alone. Some information as to the structure can be obtained from fragment ion spectra; however, an efficient and certain way to recognize and distinguish such isomers is to separate them according to their different ion mobilities.

Today, ion mobilities are predominantly measured via the drift velocities of the ions in long drift regions. A drift region for measuring ion mobility contains an inert gas (such as helium or nitrogen). The ions of the substance under investigation are pulled through the gas by means of an electric field produced by suitable DC potentials at ring electrodes, which line the drift region. The large number of collisions with the gas molecules produces a constant drift velocity $v_d$ for each ion species which is, in first approximation, proportional to the electric field strength E: $v_d = K_0 \times E$. The proportionality constant $K_0$ is called the "ion mobility" of this ion species. The ion mobility is a function of the temperature, gas pressure, type of gas, ion charge and, in particular, the collision cross-section of the ions. At the same temperature, pressure and type of gas, isomeric ions of the same charge-related mass m/z, but different collision cross-sections have different ion mobilities. Isomers of the smallest geometric dimension possess the greatest mobility and therefore the highest drift velocity through the gas. Unfolded protein ions undergo more collisions than tightly folded proteins. Protein ions which are unfolded, or partially folded, therefore arrive at the end of the cell later than strongly folded ions of the same mass. But structural isomers, for example proteins with glycosyl, lipid or phosphoryl groups at varying sites, also have different collision cross-sections, which allows them to be distinguished by measuring their ion mobility.

In modern chemical and biological research, it has become more and more important to have knowledge about the folding structures of molecules, which often can be determined by mobility measurements of their ions. Therefore devices to measure the mobility of ions have been incorporated into mass spectrometers, in particular to combine measurement of the charge-related mass of ions with measurement of collision cross-sections. The folding structures strongly influence the mechanism of action and thus the effect of the molecules in the living organism; different foldings can signify normal or abnormal functions of biopolymers in biosystems, and hence health or disease of tissue parts of even whole organisms.

A variety of information can be obtained from ion mobility measurement. It is possible to qualitatively detect simply the existence of different conformational isomers, for example. More detailed measurements of the mobility spectra can be used to quantitatively analyze mixtures of structural isomers or conformational isomers (as part of quality control for the production of chemicals, for example). Folding patterns can be confirmed or disproved by calibrated ion mobility measurements with determination of exact mobility values and comparisons with computed collision cross-sections.

A number of academic research groups have coupled ion mobility spectrometry with mass spectrometers. A pressure range of a few hectopascals has been adopted almost universally for the mobility drift region; the drift region for higher mobility resolutions is up to four meters and more, and electric field strengths of 2,000 volts per meter and more are applied. In this pressure range, the drifting ions appear to form hardly any complexes with other substances, so the mobilities of the ion species can be measured without any interference, unlike mobility measurements at atmospheric pressure. But in the long drift regions, the ions also diffuse radially over long distances, and therefore quite large diameters have to be chosen for these drift regions.

The ions are usually introduced into the drift region in the form of temporally short ion pulses, as a result of which they initially adopt the shape of spatially small ion clouds, which are pulled through the drift region by the electric field. In the gas of the drift region, these ion clouds are subject to diffusion into the surrounding space, the diffusion being caused by collisions statistically distributed in terms of spatial directions and kinetic energies due to molecular Brownian motion. The diffusion takes place in both the forward and the backward direction, and also at right angles to the drift region. The gas in the drift region is often kept at temperatures of between about 150 and 300 degrees Celsius, but can also be greatly cooled for special experiments. The mobility resolving power $R_{mob}$ ("mobility resolution" for short) is influenced predominantly by this diffusion broadening of the ion clouds, especially for long drift regions and high electric field strengths; all other influences, such as the space charge, are negligibly small. The part of the mobility resolution determined by the diffusion broadening is given by the equation $$R_d = \sqrt{\frac{zeEL_d}{kT \ln 2}},$$

where z is the number of elementary charges e, E the electric field strength, $L_d$ the length of the drift region, k the Boltzmann constant and T the temperature of the gas in the drift region. The mobility resolution is defined as $R_{mob} = K_0/\Delta K_0$, where $\Delta K_0$ is the width of the ion signal of the mobility $K_0$ at half height, measured in units of the mobility. The part $R_d$ of the mobility resolution given by the diffusion is not dependent on either the type or pressure of the gas in the drift region; the mobility $K_0$ itself, however, does depend not only on the temperature, but also on the pressure and type of the gas.

As is known from very early work on charged particles from the end of the 19th century, this type of ion mobility measurement in a non-moving drift gas can be modified by a counter-flow of the gas in the drift region, resulting in a shortening of the drift region. In this case, arbitrarily high mobility resolutions can, in theory, be achieved for ions of a selected mobility, which are held over a long period in equilibrium between the electric force of attraction and the viscous drag in the gas; but unfortunately only in theory. For practical applications there are fundamental limits which make the method unusable because the diffusion of the ion cloud, which is in equilibrium between the electric force of attraction and the viscous drag in the gas, does not stop either radially or axially at any time. Therefore, the ion cloud drifting apart by diffusion quickly exceeds all instrument dimensions.

Compared to the numerical values for mass resolutions in mass spectrometry, the mobility resolutions which can be achieved in practice are generally very low. The first commercial ion mobility spectrometer for bioorganic ions, which is very successful on the market, has a mobility resolution of only $R_{mob}=10$ to 15. With a mobility resolution of $R_{mob}=10$, two ion species whose collision cross-sections differ by only 20 percent can be readily separated.

Only highly specialized academic working groups have, as yet, been able to achieve significantly higher mobility resolutions of between $R_{mob}=60$ and 100, in rare individual cases up to $R_{mob}=150$, with drift lengths roughly between two and six meters and field strengths between 2,000 and 4,000 volts per meter, making it possible to differentiate between ion species whose mobilities differ by only one to three percent. Ion mobility spectrometers with a resolution above $R_{mob}=60$ shall be called "high resolution" here.

Since long mobility drift regions also entail strong transverse diffusion, longer drift regions must have a large diameter in order that the ions do not arrive at the wall electrodes. A well-tried method is therefore to guide the ions back to the axis of the drift region once they have passed through part of the drift region, after about two meters, for example. This is done using so-called "ion funnels". These consist of a large number of stacked ring electrodes, closely spaced by only a few millimeters apart, whose aperture diameters taper continuously from the diameter of the drift region, between 30 and 40 centimeters, for example, to around two to five millimeters and thus form a funnel-shaped enclosed volume. The two phases of an RF voltage, usually of several megahertz and between a few tens of volts and one hundred volts, are applied alternately to the apertured diaphragms, thus generating a pseudopotential which keeps the ions away from the funnel wall. A DC electric field is superimposed on the RF voltage by a DC voltage gradient, and this electric field pushes the ions slowly to the narrow exit of the funnel and through it. It has been found that such ion funnels do not measurably reduce the mobility resolution of a long drift region.

Ion funnels are not only used to guide the ions back to the axis of the drift region in ion mobility spectrometers; they are also used in mass spectrometers in general to capture larger ion clouds and thread them into narrow ion guides. As can be seen in the example shown in FIG. 2, such ion funnels are often found in mass spectrometers with an electrospray ion source, in which ions generated outside the vacuum system are transferred, together with a curtain gas, through inlet capillaries into the vacuum, where they are captured by ion funnels and freed of most of the curtain gas. As shown schematically in FIG. 2, some mass spectrometers even contain two such ion funnels, placed in series, in order to quickly move from a region with higher pressure of a few hectopascals at the end of the inlet capillary to a region with lower pressure of between about $10^{-4}$ and $10^{-2}$ pascal. Inside these ion funnels exists a focused flow of the curtain gas, which under circumstances can even have all the characteristics of a jet flying at the speed of sound, due to the adiabatic cooling.

It should be briefly mentioned here that such gas flows are also often found in other types of ion guide, particularly if they are close to ion sources, such as the ion guide (11) of FIG. 2. Such ion guides can simply have the form of hexapole or quadrupole rod systems, which are operated with RF voltages, for example. A series of ion-optical lenses can also form an ion guide. Ion guides can be constructed with axial electric fields to actively push the ions through, although such ion guides are rare, as yet, except for ion funnels.

It is known that the conditions for conformational changes which occur by changes of the gas temperature can also be studied in ion mobility spectrometers. If, for example, the gas temperature is continuously increased in a region where the prevailing gas density and the dwell time of the ions allow that they can largely attain the temperature of the gas, and if the mobilities are measured as a function of the temperature, it is then possible to investigate transitions from one type of folding to another. It is particularly possible to determine the energy thresholds which have to be exceeded for conformational changes. Very fast cooling of the ions from a very hot state allows the most probable conformational states to be frozen and thus measured. Slow cooling of previously hot ions can often be used to find the conformational isomer with the lowest energy level.

For many biochemical applications, particularly protein chemistry applications for determining conformational states, a mass-accurate mass spectrometer, for example a time-of-flight mass spectrometer with an integrated mobility measuring station having a mobility resolution of $R_{mob}=30$-50 would already be eminently suitable. This could separate ions with mobilities differing only by some three to six percent. Conformational changes are often accompanied by mobility changes of at least this order of magnitude. This range of $R_{mob}=30$-50 shall therefore be called "medium-resolution" in the following, while the region below $R_{mob}=20$ shall be considered to be "low-resolution". The region with $R_{mob}>60$ has already been defined above as "high-resolution".

It should be noted here, that mobility resolution is essential for many applications, but mobility precision might be even more essential. Mobility precision is the precision for the determination of the mobility $K_0$. The precision characterizes how well the mobility constant for a single ion species can be reproduced. With a good mobility spectrometer of $R_{mob}=50$, the mobility constant $K_0$ may be determined with a precision of 0.2 percent or even better.

Several arrangements of mobility spectrometers are known where the ions are mass-analyzed in a high-resolution time-of-flight mass spectrometer, in addition to the measurement of their mobility, the aim being to obtain mass spectra and mobility spectra of the ion mixtures at the same time. It is of particular interest if daughter ion spectra of ions of a selected mobility can also be acquired in order to obtain additional information on the structure of the ions.

For such combinations, current types of high-resolution ion mobility spectrometer have the disadvantage of being several meters long. Such a solution is unfavorable for commercial instruments. Even medium-resolution ion mobility spectrometers with a straight drift region are about one meter long. For the construction of small, medium- to high-resolution mobility analyzers, a solution is required which reduces the overall length without diminishing the mobility resolution.

In the publication WO 2004/109741 A2 (John Noyes, priority date Jun. 6, 2003) methods and arrangements have been proposed where ions can be introduced into a laminar gas flow, kept inside the laminar gas flow by an ion guide, and pushed over the maximum of an opposing electric field of a potential barrier. Ions which are pushed over are separated from ions which are held back by the electric field opposing the gas flow. By changing the barrier, the boundary between the ions pushed over and those held back can be varied. The publication does not give a definition of the term "laminar"; however, the disclosed system is designed to produce a laminar gas flow in a tube. The tube is located inside an RF quadrupole rod ion guide and is manufactured from a high-resistance conducting dielectric material so that the RF field can penetrate the tube wall and keep the ions in the axis of the laminar gas flow. This tube and the ion guide are the essence of the invention disclosed in the publication which is completely oriented toward the gas flow in this tube with corresponding parabolic velocity profile; see here FIGS. 8 and 9 and the accompanying descriptions, for example.

Although no methods for acquiring mobility spectra are presented in this publication, it is nowadays obvious that mobility spectra can be acquired with this arrangement. However, since the publication gives no measured values at all regarding the separation of ions at the barrier, it is not possible to infer from this publication whether, and how well, the separation of ions of different mobility would work and whether a sufficiently good mobility resolution could be achieved. A fundamental disadvantage of the method presented in this publication is that a parabolic velocity profile prevails in a laminar gas flow through a tube, so only the ions on the axis experience the maximum friction, with which they can be pushed over the barrier. The RF multipole rod system must therefore produce very good focusing of the ions on the axis of the tube in order to offset this disadvantage.

In general, electric field barriers are connected with electric potential distributions, usually with potential barriers. The maximum of the electric field component of a potential barrier in opposite direction to the flowing gas will be simply called "field maximum" or "field barrier" below. The field maximum is identical to the steepest part of the positive slope of the potential distribution of the potential barrier in the direction of the gas flow.

A publication by J. S. Page et al., "Variable low-mass filtering using an electrodynamic ion funnel", Journal of Mass Spectrometry. 2005, 40: 1215-1222 elucidated the use of an ion funnel to suppress ions of low mass in the range up to about 500 daltons, which often form a strongly interfering background in mass spectra. The authors hold back light ions below an adjustable mass threshold at the end of the ion funnel by means of an adjustable potential barrier at a ring diaphragm and filter them out of the ion current. To explain this effect, the authors propose that essentially the gas flow in the ion funnel pushes the ions over the field barrier connected with the potential barrier as a function of their mobility, and that the mobility of the light ions here gives the impression of a mass dependence because, for light ions, the mobility is mainly inversely proportional to the mass of the ions. The authors have made no attempt to use this effect to measure the ion mobility, however, despite extensive measurements on the suppression of light ions.

SUMMARY

In accordance with the principles of the invention, a jet of ion-containing gas is produced by free expansion of the gas through a nozzle into a vacuum and used to push ions of sufficiently low ion mobility over an electrical field barrier, thus sorting the ions according to their mobilities. No ion guide is necessary if the field barrier is located adjacent to the exit of the nozzle. If the field barrier is located in some distance from the nozzle, an ion guide may serve to canalize the ions to the field barrier. The ion guide should be shaped so as to minimize any hindrance to the free expansion of the gas outside the jet. These ion guides can take the form of ion funnels, but also of multipole rod systems. The ion guides serve to hold the ions together in the radial direction; propulsion in the axial direction is not important as long as the ions are kept entrained by the gas jet. For ion funnels, propulsion in axial direction is required, because ions can leave the gas jet inside the wide part of the ion funnel and have to be redirected into the gas jet.

In another embodiment, a jet of ion containing gas is formed by adiabatic expansion of the gas through a Laval nozzle. The jet is used in conjunction with an electric field barrier to sort the ions into those which are pushed by the jet over the field barrier, and those which are held back by the field barrier. To make the gas expand through the nozzle, a pressure difference at both sides of the nozzle has to be maintained, for example by a differential pumping system.

In still another embodiment the current of ions which are pushed over the field barrier by the gas jet, is measured with constant replenishment of ions from the ion source, as a function of the height of the voltage at the electrodes which generate the barrier. If the height of the field barrier is changed continuously or incrementally, a total ion current curve, which represents an integral over the mobility spectrum, is measured at the ion detector. Differentiation of this total ion current curve with respect to the height of the potential barrier provides the mobility spectrum of the ions. This method of acquiring mobility spectra can be calibrated by using ions of exactly known mobility; absolute values of ion mobilities can then be determined by calibrated spectrum acquisition methods.

If the ion current is fed to a mass analyzer and measured in the form of a series of mass spectra as a function of the height of the potential barrier, for example using a time-of-flight mass spectrometer with orthogonal ion injection, individual ion current curves for ions of individual mass ranges can be derived from this series of mass spectra, The differentiation of these curves then provides ion mobility spectra for individual mass ranges. The mass ranges can cover ions of several masses, such as the masses of an isotopic group, or only ions of a single mass.

In yet another embodiment, the ion guide is used as an ion storage device from which, after the filling is complete, the ions are blown over a continuously or incrementally diminishing field barrier and on to the ion detector by the gas jet. This allows a mobility spectrum from low to high mobilities to be measured directly, i.e. without differentiation.

This method can also be used to measure ion mobility spectra for individual mass ranges if a mass spectrometer is connected as the mass analyzer. Since, in this case, the ions can be fed to the mass spectrometer separated according to their mobility, ions of selected mobilities can be fragmented by this method in suitable mass spectrometers, allowing measurement of fragment ion spectra of ion species separated according to their mobility and mass.

These methods result in a surprisingly good mobility resolution which, according to all current knowledge on mobility separation principles, would not be expected. According to initial, still very rough experiments, the mobility resolution is in the region of better than $R_{mob}=35$; much higher mobility resolutions seem achievable. Also surprisingly, gas jets produced by pressure differences of below a few tens of pascals or lower can be used advantageously.

The ion guides here serve to canalize the ions to the field maximum of the potential barrier in such a way that their lateral spread is limited. For higher potential barriers, i.e. for stronger opposing fields, a stronger lateral guidance of the ions to the field barrier can be achieved by increasing the RF voltage at the ion guide synchronously with the potential barrier. Instead of increasing the RF voltage, its frequency can be decreased.

Some mass spectrometers already contain ion funnels or other suitable ion guides and also differential pumping systems, so it is possible to implement such a measuring station for ion mobilities in these mass spectrometers without much development effort.

The field barrier can be either a DC barrier or the barrier of a pseudopotential. The barrier can be increased or decreased continuously or incrementally to acquire the integrals over the mobility spectra.

The ion guide can be a multipole rod system, a system of diaphragms with apertures, or an ion funnel, all operated with RF voltages. But it can also be an ion-optical lens system to which only DC voltages are applied. In order to hinder the gas jet as little as possible, the pole rods or diaphragms can have special shapes which conduct the gas outside the gas jet as efficiently as possible to the pumps without disturbing the gas jet between nozzle and field barrier.

The methods and apparatus according to the invention achieve an unexpectedly good mobility resolution. One reason for the high mobility resolution is probably that the gas jet in the vicinity of the field barrier has the same velocity everywhere, i.e. it does not have a parabolic velocity profile as in publication WO 2004/109741 A2. A favorable design of the field barrier in the radial direction also contributes to the high mobility resolution. A further reason is the almost complete absence of diffusion broadening of the ion signals. Any diffusion of ions inside the gas before the barrier has no effect. After crossing the barrier, the now sorted ions should be fed as quickly as possible to the ion detector or the mass analyzer in order to keep the diffusion low. The temperature of the adiabatically cooled gas jet is very low in the critical region of the barrier and from there to the ion detector or mass spectrometer, which greatly reduces the diffusion.

are chosen such that the field barrier is built up directly at the exit of the Laval nozzle (6) so that all ions are pushed against the field barrier with equal force. The passing ions are collected by an ion funnel (8), separating the ions from the remaining gas and guiding them to the ion detector (21) in a separate pumping chamber pumped by pump (24).

Figure 8:
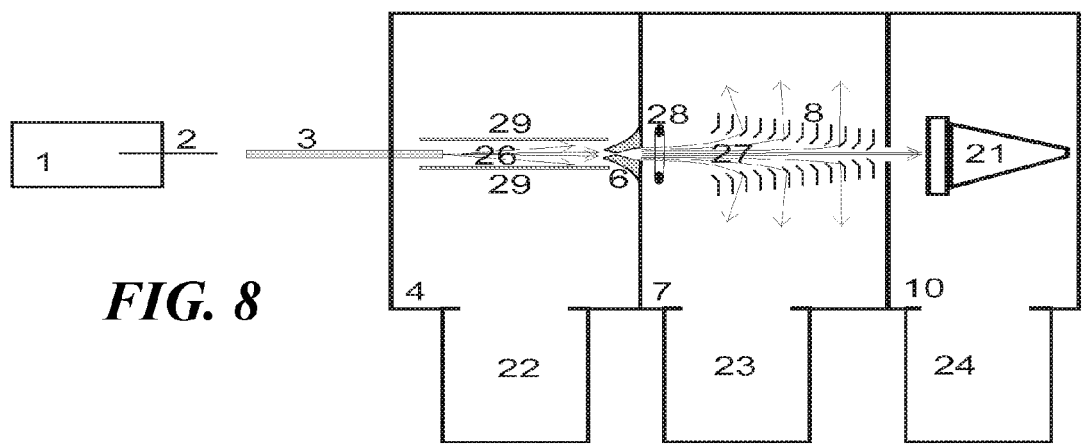
FIG. 8 schematically presents a somewhat more sophisticated ion mobility spectrometer than shown in FIG. 6, using a Laval nozzle (6) at an intermediate pressure. The primary gas stream (26) from the entrance capillary is directed towards the Laval nozzle (6) surrounded by a skimmer. The ions inside the gas stream (26) are canalized and guided towards the center of the Laval nozzle (6) by the pseudopotential of an RF quadrupole rod system (29). The Laval nozzle is operated by the back-up pressure of the gas stream (26). The gas jet (27) formed by the Laval nozzle (6) here passes ring electrode (28) which creates the field barrier by suitable voltages. Location, size and distance of the ring electrode (28)
Figure 9:
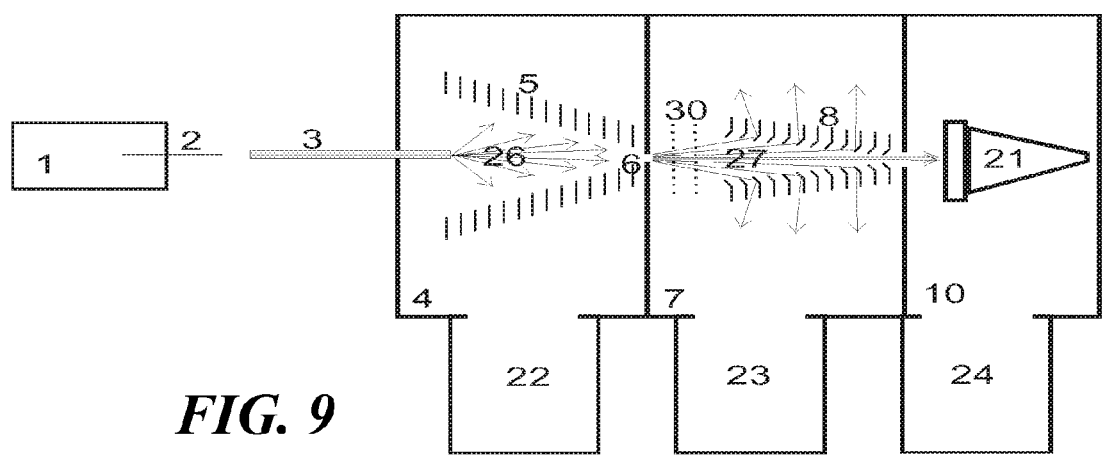

In FIG. 9, the ring electrode (28) of FIG. 8 is replaced by two fine grids (30) which span the electric field, serving as barrier, between them, or between the first grid and the nozzle (6).

Figure 1:
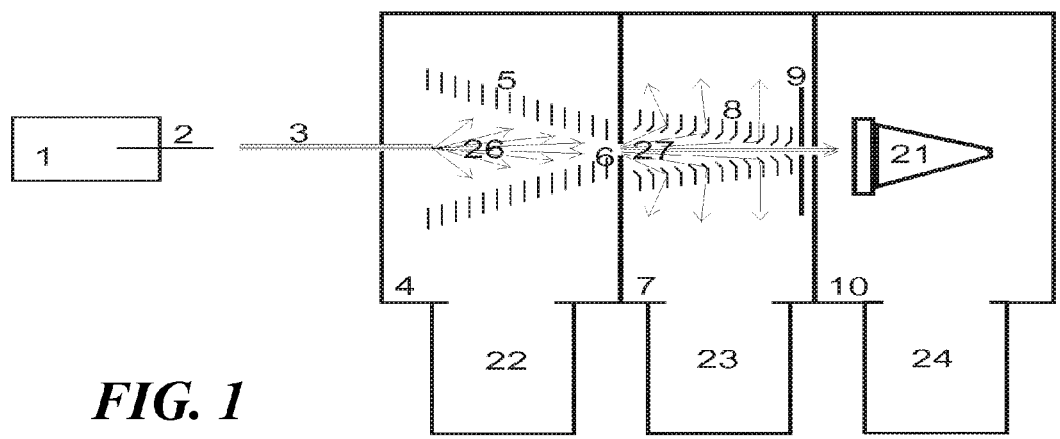
FIG. 1 schematically represents an ion mobility spectrometer according to this invention, with an electrospray ion source (1, 2) outside the vacuum system, an inlet capillary (3) for curtain gas and ions, two ion funnels (5, 8), an ion detector (21) and a differential pumping system (22, 23, 24). Passing the nozzle (6) at the end of the first ion funnel (5), the gas expands adiabatically into the vacuum chamber (7) of the second pumping stage, forming the gas jet (27). The apertures of the diaphragms of the second ion funnel (8) have skimmers which guide the impinging gas of the outer regions of the gas jet (27) to the outside in order to maintain an unhindered gas jet inside the ion funnel (8). The ions are canalized inside the gas jet (27) by the second ion funnel (8) and transmitted virtually without any losses to the field barrier at the ring diaphragm (9). The ions are propelled by the gas jet (27). To acquire mobility spectra, the DC electric potential at the ring diaphragm (9) at the end of the second ion funnel (8) is increased continuously or incrementally, resulting in more and more ions from the ion current of the ion source being repelled due to their then excessive mobility, and thus filtered out. The integral of the mobility spectrum of the ions under investigation is thus measured at the detector (21). Differentiation provides the mobility spectrum.
Figure 2:
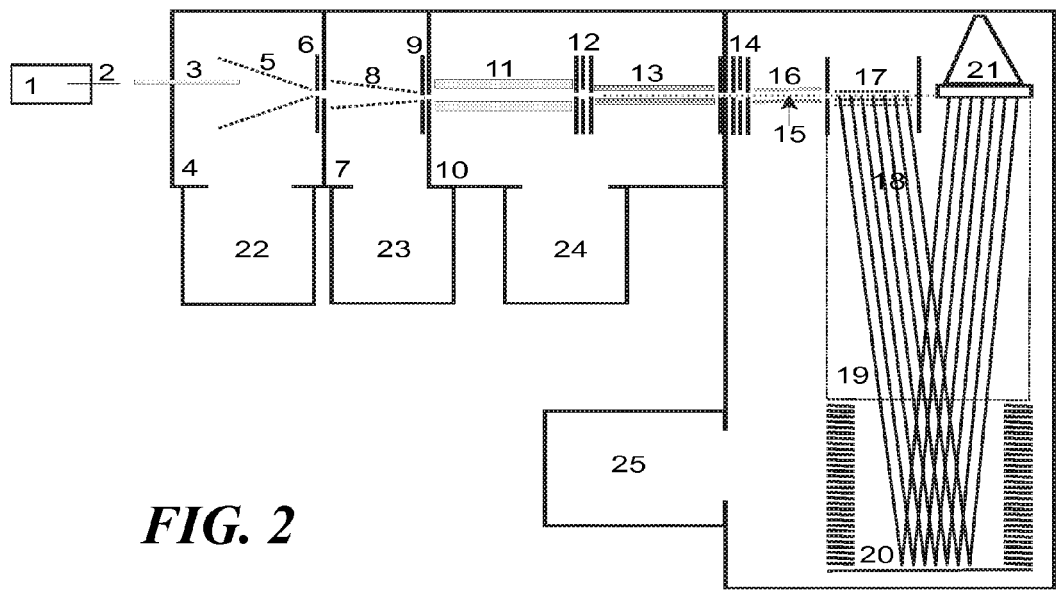
FIG. 2 is a schematic representation of an orthogonal time-of-flight mass spectrometer (OTOF) with an electrospray ion source which contains the mobility spectrometer elements shown in FIG. 1. With the OTOF, mobility spectra for the individual ion species can be measured.
Figure 10:
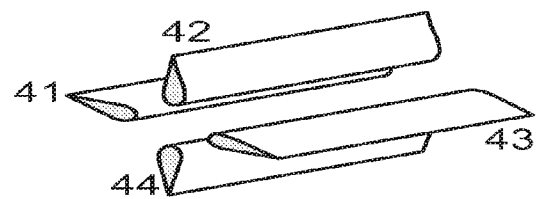

FIG. 10 exhibits a quadrupole ion guide with wing-like rods (41 to 44) which can replace the ion funnel (8) in FIGS. 1 and 2.

DETAILED DESCRIPTION

While the invention has been shown and described with reference to a number of embodiments thereof, it will be recognized by those skilled in the art that various changes in form and detail may be made herein without departing from the spirit and scope of the invention as defined by the appended claims.

The invention provides a method which uses an ion-containing gas jet, formed by adiabatic expansion of the gas through a nozzle, in conjunction with a field barrier to sort the ions into those which can be pushed over the field barrier and those which are held back. To make the gas expand through the nozzle, a pressure difference at both sides of the nozzle has to be maintained, e.g. by a differential pumping system. The nozzle may be formed simply as a hole in the wall between two such pumping chambers. A Laval-type nozzle helps to form a nicely directed gas jet with uniform molecule velocities across the jet. The field barrier is preferably located opposite the nozzle across the central jet region.

In contrast to the prior art presented in publication WO 2004/109741 A2, in which ions are pushed over an electric field barrier by a laminar gas flow in a tube necessarily requiring an ion guiding field to hold the ions in the axis of the laminar flow, the present invention does not use the gas flow in a tube with its parabolic velocity profile, but uses instead a gas jet which is formed by the expansion of gas freely and adiabatically through a nozzle by a pressure difference. Within a nicely formed gas jet, for instance by a Laval nozzle, the gas molecules leaving the nozzle all have the same velocity and thus show an even velocity profile across the jet. This results in a surprisingly high mobility resolution. In its simplest but highly effective embodiments, this invention does not even require any ion guide up to the field barrier, which is a prerequisite in WO 2004/109741 A2.

The invention presented here furthermore uses this sorting of ions into those which can be pushed over the field barrier and those which are held back as the basis for methods to acquire ion mobility spectra, which then, in turn, allow the absolute values of ion mobilities to be determined after a suitable calibration with high precision of much less than one percent standard deviation.

Figure 6:
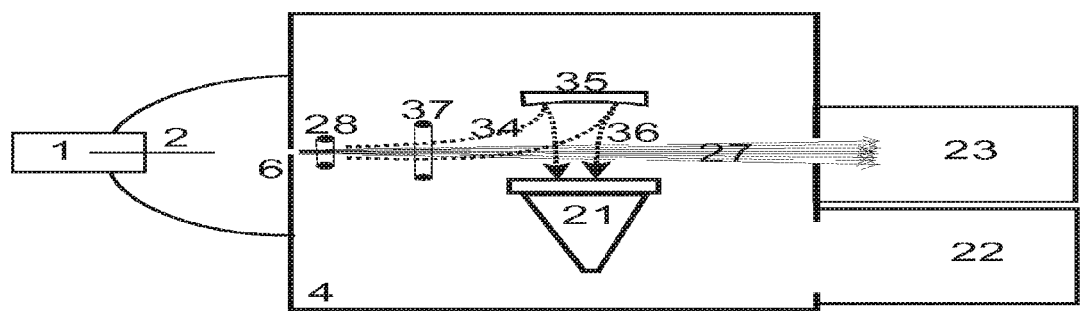
FIG. 6 presents a rough scheme of a most simple ion mobility spectrometer. The arrangement (1, 2) symbolizes a usual electrospray unit comprising spray capillary, housing, curtain gas supply, and electrode arrangement to draw a large part of the ions into the nozzle (6) which is used here instead of an entrance capillary. Nozzle (6) is a tiny Laval nozzle with only a few micrometers diameter at the narrowest part, sucking a few liters of curtain gas per minute and generating a supersonic jet (27) directed into the pump chamber (23), where the overwhelming part of the jet is completely absorbed by a turbomolecular pump. At the exit of the Laval nozzle (6), all molecules of the jet have the same velocity. A voltage at the ring electrode (28) generates a field barrier directly at the exit of nozzle (6). The field barrier holds back all ions in the curtain gas not having sufficiently low mobility, and these ions are necessarily discharged at the inner surfaces of the Laval nozzle (6). The passing ions (34) are accelerated by a second ring electrode (37) towards the detector system, comprising a conversion dynode (35) and a channeltron plate secondary electron multiplier (21). The ions (34) generate electrons at the conversion dynode (35), and the electrons (36) are accelerated towards the detector (21).

An extremely simple embodiment of the invention without any RF ion guide is exhibited in FIG. 6, presenting a rough scheme of an ion mobility spectrometer. The arrangement (1, 2) shown symbolically here is a conventional electrospray unit comprising spray capillary, housing, curtain gas supply, and electric field arrangement to generate ions and to draw a large part of the ions into the nozzle (6) which is used here instead of the usual entrance capillary. Nozzle (6) is a tiny Laval nozzle with only a few micrometers diameter at the narrowest part, sucking a few liters of curtain gas per minute. Laval nozzles of this size can be produced by electron beam drilling, or by UV-Laser beam drilling. The Laval nozzle (6) generates a supersonic jet (27) which is directed across chamber (4) into the pump chamber (23), where a significant part of the jet is completely absorbed by a turbomolecular pump. A second pump (22) maintains a suitably low pressure in chamber (4). At the exit of the Laval nozzle (6), all molecules of the jet have the same velocity. A voltage at the ring electrode (28) generates a field barrier, which can be built up tightly at the exit of nozzle (6) by choosing the right size and distance of ring electrode (28). The field barrier holds back all ions in the curtain gas not having sufficiently low mobility, and these ions are necessarily discharged at the inner surfaces of the Laval nozzle (6). The passing ions (34) are accelerated by a second ring electrode (37) towards the detector system, here consisting of a conversion dynode (35) and a channeltron plate secondary electron multiplier (21). The ions (34) generate electrons at the conversion dynode (35), and the electrons (36) are accelerated towards the detector (21). If the ion current from the electrospray ion source is kept constant, the integral mobility spectrum can be measured by changing the voltage at the ring electrode (28) generating the field barrier.

Figure 7:
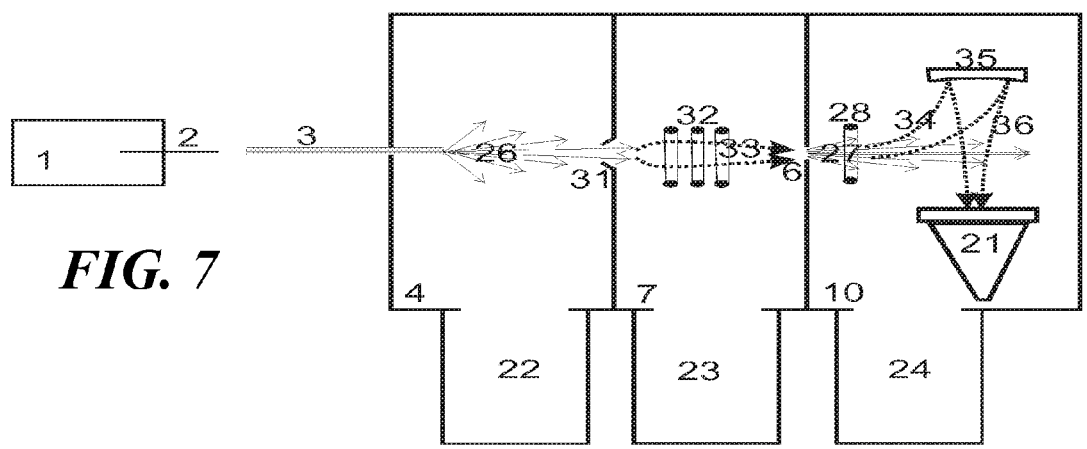
FIG. 7 exhibits another simple arrangement for an ion mobility spectrometer according to this invention without any ion guides, wherein the jet is generated at much lower pressures. The primary gas stream (26) from the entrance capillary of the electrospray ion source (1, 2) is directed towards an aperture (31) with a skimmer, letting pass a little gas with most of the ions into pumping chamber (7). In chamber (7), the ions (33) are attracted by the lens system (32) and focused onto nozzle (6). The expanding gas jet (27) from the nozzle (6), containing most of the ions, passes a ring electrode (28). A voltage at the ring electrode (28) provides the field barrier at the exit of the nozzle (6). Passing ions (34) are accelerated towards the conversion dynode (35), and the secondary electrons (36) generated here are measured by the detector (21).

Another simple embodiment is shown in FIG. 7, comprising a conventional inlet capillary (3) and generating the jet (27) at much lower pressure. The ions are generated by the electrospray ion source (1) symbolically shown with spray capillary (2) only, and the ions are drawn by a curtain gas through the inlet capillary (3). The outflow (26) of the inlet capillary is directed inside chamber (4) towards an aperture (31) with a skimmer that reflects the largest part of the gas stream (26) which is pumped away by pump (22). A voltage at the skimmer (31) attracts a large part of the ions and makes them pass through the skimmer aperture. This type of skimmer arrangement was exclusively used until the invention of the ion funnel; many commercial mass spectrometers still today incorporate this skimmer arrangement. Within chamber (7), the ions (33) passing the skimmer aperture (31) are attracted by the lens system (32) and focused into the nozzle (6). The gas pressure in chamber (7) should be still high enough to create the gas jet (27) by expansion through nozzle (6) into the vacuum of chamber (10). The gas jet (27) from the nozzle (6) passes a ring electrode (28) which provides the field barrier by a suitable voltage between ring electrode (28) and nozzle (6). Here also the field barrier should be formed directly at the exit of nozzle (6) so that all ions are pushed against the field barrier. Ions (34) passing the field barrier are accelerated by several kilovolts towards the conversion electrode (35), and the secondary electrons (36) generated here by impinging ions are measured by the channel plate detector (21).

A somewhat more elaborated version of the same principle is schematically shown in FIG. 8, applying two ion guides to catch and guide the ions, but not between jet forming nozzle and field barrier. The primary gas stream (26) from the entrance capillary is directed towards a Laval nozzle (6) surrounded by a skimmer. For the sake of clarity, the Laval nozzle in FIG. 8 is shown somewhat enlarged out of scale. The ions within the primary gas flow (26) from the entrance capillary (3) are caught and guided towards the center of the Laval nozzle (6) by an RF quadrupole ion guide (29). The Laval nozzle is operated by the back-up pressure of the gas stream (26). The gas jet (27) formed by the Laval nozzle (6) passes the ring electrode (28) which creates the field barrier by suitable voltages. Also here it is favorable to generate the field barrier directly at the exit of nozzle (6), by a suitable choice of size and shape of the electrode (28) and its distance from the nozzle (6). The passing ions are then collected by a second ion funnel (8), separating the ions from the gas and guiding them, by a DC voltage gradient, towards the ion detector (21) in a separate pumping chamber (10) which is pumped by pump (24). The ions are highly accelerated by several kilovolts towards the ion detector (21).

Although the electrode (28) in FIG. 8 allows creation of a favorable shape of the field barrier, for some applications it is still more favorable to simply use grids (30) to create the field barrier, as shown in FIG. 9. The field barrier can be created by voltages between the two grids (30), or even, more favorable, between the first grid and the nozzle (6), creating the field barrier directly at the exit of the nozzle (6). In FIG. 9, the ions are caught and guided in chamber (4) by an ion funnel 5, instead of the quadrupole rod arrangement in FIG. 8.

In FIGS. 6, 7, 8 and 9, the field barrier is located most favorably directly in front of the nozzle (6). During adiabatic expansion, the gas cools down to low temperatures and forms a jet in which all molecules have about the same velocity across the jet. As long as the ions are transported within this jet to the field barrier, high mobility resolution can be achieved. Therefore, it is highly preferable to generate the field barrier directly at the exit of the nozzle (6).

If the gas jet arrives at the field barrier in a short distance from the nozzle, some of the ions already will leave the jet in radial direction driven by space charge. These ions can no longer be pushed over the field barrier; they are lost for any measurement. If the field barrier is located in some distance from nozzle (6), the ions have to be strongly canalized in order to not let them escape radially.

To canalize the ions within the gas jet to the field barrier, an ion guide can be used which, however, should be designed in such a way that it does not disturb the gas jet. Restrictions or reflections of the gas flow outside the gas jet brought about by the ion guide, which could disturb the gas jet, must be avoided. In the absence of electric guiding fields, the ions would leave the gas jet driven by space charge forces in all directions. However, the radial reverse acceleration forces of the pseudopotential of the ion guide have the effect that the ions are held in the central flow region of the slightly diverging gas jet, and canalized therein up to the field barrier.

The ion guides can be multipole rod systems (as shown in FIG. 10), stacked ring electrode systems, or ion funnels (like ion funnel (8) in FIG. 1), which must, however, be designed so that they do not hinder the lateral outflow of the gas jet. The lateral outflow of the gas jet is mainly caused by friction of the gas jet with residual gas. The pole rods of the multipole rod system should therefore be kept very thin. Instead of round pole rods, the rod systems may be built, as shown for a quadrupole system in FIG. 9, by wing-shaped pole electrodes (41-44) with wide gaps for the outflow of the gas. The rounded edges of the wings then replace the pole rods; the smaller summit radius must be compensated for by higher RF voltages. The diaphragms of the ring diaphragm systems and the ion funnels can be equipped with gas skimmers which conduct the impinging gas flow to the outside, as is shown in FIG. 1 for the gas flow (27) in the ion funnel (8).

In all applications, the shape of the field barrier is essential for mobility resolution. Field barriers can be generated in different ways, for example by voltages on ring electrodes or simple apertured diaphragms or ion-optical lens systems consisting of several apertured diaphragms. The spatial potential distributions of such field barriers usually have the shape of potential saddles. However, the mobility separation does not depend on the potential saddle, but on the axial component of the electric field generated by the potential distribution. On the positive slope toward the potential saddle, the strength of the axial component of the electric field initially increases, then crosses a field maximum in the steepest portion of the positive slope before again reaching the zero value in the saddle point of the potential barrier.

While the potential obeys Laplace's equations and can only ever assume a spatial potential saddle, but never a spatial maximum or minimum, the area around the field maximum in the radial direction can assume different forms. If the axial field component in the field maximum decreases with radial distance from the axis, the field maximum in the cross-section forms a mountain peak. If it increases, however, a saddle is formed, i.e. a mountain pass. If it remains constant regardless of the radial distance from the axis, it forms, figuratively speaking, a transverse mountain ridge which can be crossed by the ions in the gas flow everywhere with the same chance because the gas flow has a homogenous velocity distribution in the vicinity of the ridge-like field maximum. It is, therefore, most favorable for achieving a high mobility resolution if the field maximum is formed as a mountain ridge where the field maximum has a radially constant height, because then the separation of the ions according to their mobility is achieved everywhere at the same mobility threshold regardless of their distance from the axis. This form of a radially extended field barrier which has the same height everywhere can, in approximation, be generated by an arrangement of several ring diaphragms with corresponding DC voltages.

In the case of such a mountain ridge, the ions are not focused toward the axis by the field in the vicinity of the field maximum. They therefore have to be prevented from escaping radially by the ion guide. To achieve this, the ion guide must extend to the field maximum. With a weak field saddle, on the other hand, there is a weak focusing of the ions by the electric field of the potential barrier; the ion guide does not then have to extend right up to the field maximum. Since the saddle of the potential barrier is located behind the field maximum, and the saddle is usually in the center of an apertured diaphragm, this most important apertured diaphragm for generating the potential barrier can even be located at some distance outside the ion guide. The field barrier can also be located inside the ion guide, however, and can be shaped by potentials at the ion guide electrodes, e.g. at ring diaphragms of the ion guides, in such a way that a good mobility resolution is achieved.

The methods for measuring mobility spectra according to this invention do not use firm potential barriers but change the potential of the potential barrier (and with it the maximum of the axial field strength) continuously or incrementally. Consequently, in the first of these methods, more and more (or if the potential barrier is reduced, fewer and fewer) ion species are filtered out of a constant ion current from an ion source at the potential barrier due to the mobility of the ion species. An integral over the mobility spectrum of the ions is thus measured. A differentiation of the integral curves gives the mobility spectrum. This first spectrum acquisition method can be used by all embodiments of the invention including those not containing an ion guide.

With this first method, the ions of high mobility, which are held back, could create a space charge cloud which would disturb the further course of the method. This can be prevented by a suitable choice of RF and DC voltages at the electrodes of the ion guide (8) which ensures that most of these ions can escape laterally. These voltages at the ion guide can then advantageously be changed simultaneously with the height of the potential barrier, on the one hand to adapt the escape of ions of high mobility which are held back, and, on the other, to adapt the strength of the lateral guidance for the ions to the height of the opposing field.

A second spectrum acquisition method can be applied only by embodiments with ion guides between jet generating nozzle and field barrier. The ion guide is used as an ion storage device, which is filled by the ion beam from the ion source by keeping a high field barrier to prevent the ions escaping. After switching off the further supply of ions, the ions assemble in the axis of the storage device on the slope of the field barrier because they are pushed by the gas jet against the field barrier and collect at different heights according to their mobility. An axial electric field in the ion guide may support the drive of the ions against the field barrier. Ions with high mobility collect at the foot of the field barrier, where only a small electric field is present; those of low mobility, on the other hand, collect just below the field maximum. If the field barrier is now constantly lowered, one ion species after the other can be blown by the gas jet across the field maximum and escape in the direction of the ion detector. The mobility spectrum is thus measured directly, without the need for a differentiation. This second method is limited to about $10^7$ ions, which can be stored in the ion guide without space charge effects having a noticeable disturbing effect. This limits the dynamic range of measurement, but to a remarkably large measurement range. By repeating the spectrum acquisition measurements several times, the dynamic range can be increased even further, however.

FIG. 1 is a schematic representation of an ion mobility spectrometer which can be used for both types of spectrum acquisition according to this invention because of the ion guide (8) between the nozzle (6) and the field barrier generated by the apertured diaphragm (9). A conventional electrospray ion source (1, 2) outside the vacuum system supplies a mixture of ions together with curtain gas through inlet capillary (3) into a first vacuum chamber (4). Two ion funnels (5) and (8) in two vacuum chambers (4) and (7), and one ion detector (21) in vacuum chamber (10) are differentially evacuated by the vacuum pumps (22, 23, 24). The first ion funnel (5) guides the ions to the nozzle (6) which generates the gas jet (27) in chamber (7). Within the gas jet (27), the ions are kept in the axis by the second ion guide (8). Ion guide (8) is here shown to be an ion funnel with skimmers at the apertured diaphragms, but this ion guide also can be a special wing-type quadrupole ion guide as shown in FIG. 10. The potential barrier is preferably generated by a DC voltage at the ring diaphragm (9) at the end of the second ion funnel (8). The gas jet (27) blows the ions against the field barrier generated by the potential barrier. For the first spectrum acquisition method, the integral of the mobility spectrum is measured by increasing continuously the DC voltage for the potential barrier; and differentiating the ion current with respect to the potential barrier height to give the mobility spectrum. For the second spectrum acquisition method, the ion guide (8) is filled with ions, the further supply of ions from the ion source is stopped, and the mobility spectrum is directly measured by decreasing the field barrier.

Figure 3:
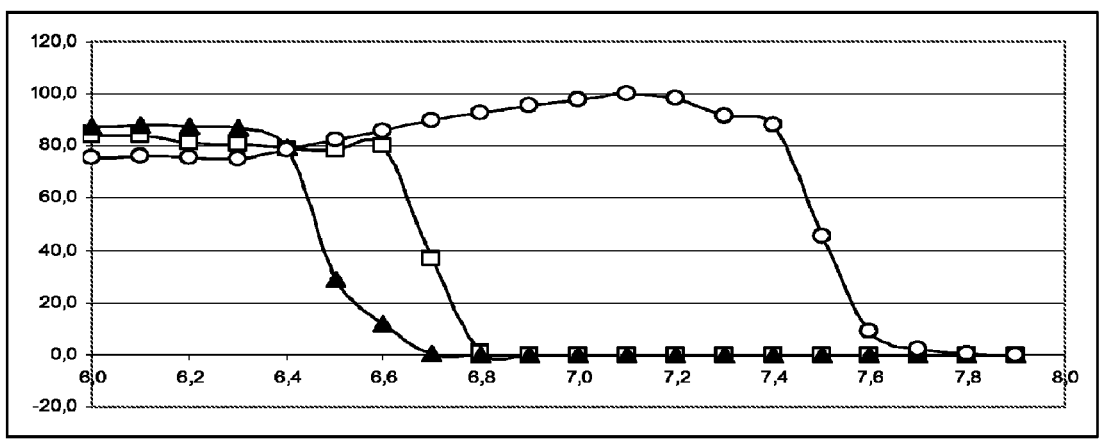
FIG. 3 shows the curves of the integral ion currents for a mixture of the doubly charged ions of bradykinin and angiotensin II, and the singly charged ions of the peptide Gly-Arg-Gly-Asp-Ser, plotted against the voltage at the ring diaphragm (9) of FIG. 2. The ion currents were extracted from a series of mass spectra which were acquired by incrementally increasing the potential barrier at the ring diaphragm (9).
Figure 4:
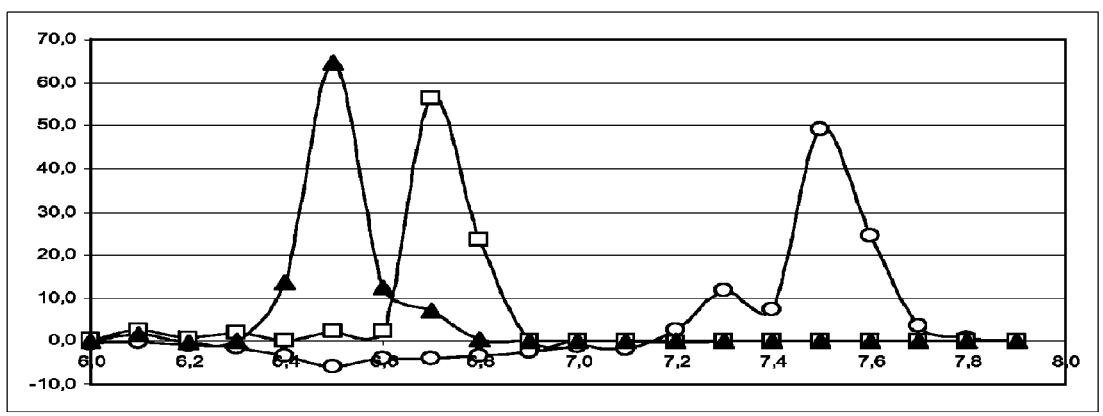
FIG. 4 was derived by differentiating the integral curves from FIG. 3, and shows the mobility spectra of these three ion species. Despite the coarse incremental steps selected for the potential barrier and despite little optimization work, the mobility resolution is in the medium range above $R_{mob}=35$. The singly charged peptide exhibits a mixture of two different conformational forms, which differ in their mobility.
Figure 5:
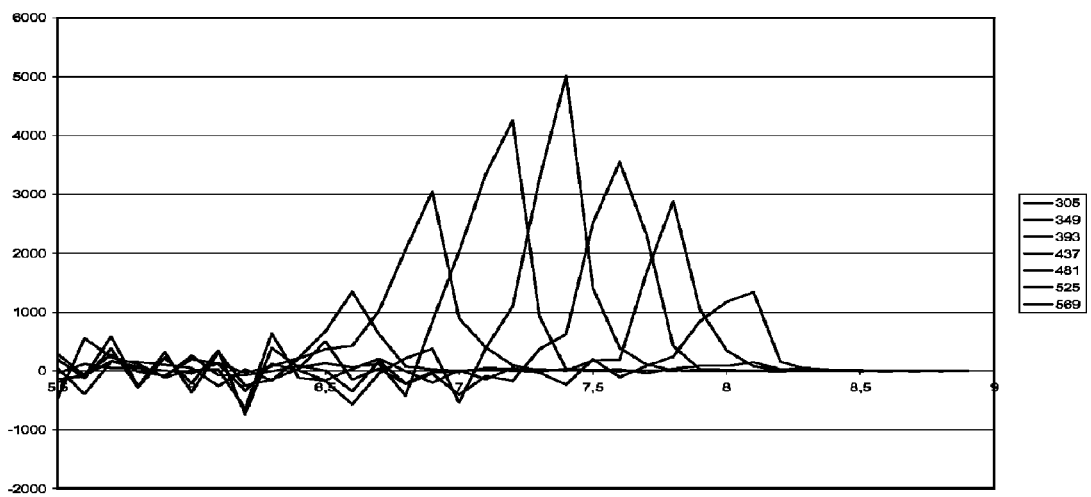
FIG. 5 shows the mobility spectra of a series of polyethylene glycoles (PEG 400), which differ not only in their mass, but also in increasing collision cross sections of the molecules and thus in their mobilities. The ions in the maximum of the distribution have a mass of 437 daltons.

Most of the embodiments described above including that of FIG. 1 can be coupled with mass spectrometers. An example is the arrangement according to FIG. 2, in which a time-of-flight mass spectrometer with orthogonal ion injection is coupled to the device used for measuring ion mobilities. The coupling here contains further ion guides (11, 13) and lens systems (12, 14), which form a thin ion beam (15). The time-of-flight mass spectrometer contains a pulser (17), which pulses out a section of the thin ion beam (15) perpendicular to the previous direction of flight of the ions and strongly accelerates it, and sends it as an ion beam (18) with high mass resolution to an ion detector (21) via an energy focusing reflector (20). There are several types of such time-of-flight mass spectrometers on the market; their operation is known to the specialist. Mass spectra can be acquired with high acquisition frequency of five to ten kilohertz. From series of mass spectra, acquired by changing the height of the potential barrier at the diaphragm (9), the ion current profiles for individual masses or mass ranges as a function of height of the potential barrier can be extracted which, depending on the method, represent the mobility spectra of the ions either directly or as an integral. In FIG. 3, the integrals of the mobility spectra of individual mass ranges can be seen as they are obtained using the first method. Their differentiation then results in the ion-mass-specific mobility spectra shown in FIG. 4.

Using a commercial mass spectrometer with two ion funnels in the inlet region, as in FIG. 2, mobility resolutions of $R_{mob}=40$ were obtained after only a short optimization, without changing the mechanical arrangement, and despite the relatively coarse potential steps selected. It can be expected that further optimizations will lead to higher resolutions. Further optimizations may concern the shape of the aperture (6), the pumping capacities of the differential pumping stages and hence the pressure difference at the aperture (6), the shape of the apertured diaphragms in the ion funnel (8) and, in particular, replacement of the single apertured diaphragm (9) by several diaphragms, whose shapes and voltages allow the generation of a field barrier with the desired shape.

The reason for the surprisingly high mobility resolutions has not yet been researched in detail. There is some degree of certainty that the shape of the field barrier, the low temperature of the adiabatically cooled gas jet, and the homogeneous velocity of the molecules in the relatively small region of the potential barrier play a role. The central region of the gas jet does not form a flow with a parabolic velocity profile in the ion guide; instead, an equal mean velocity of all molecules across the gas jet prevails in the vicinity of the potential barrier; and this velocity has a very narrow velocity distribution. The narrow spread of the velocities is the result of the adiabatic cooling of the gas during its expansion. The large number of collisions which the ions undergo with gas molecules of almost identical velocity means that such a gas jet causes a relatively equal pressure on all ions with the same collision cross-section. If the height of the field barrier is changed, and if the field barrier has the same height everywhere radially (the shape of a mountain ridge), the change will become effective for all ions of the same mobility simultaneously, regardless of how far an ion is from the axis of the central flow region. This causes all ions of the same collision cross-section from a small region of the ion beam to be pushed relatively synchronously up the positive slope of the field in front of the potential saddle and over the field maximum. This results in a high mobility resolution.

A further reason for the high mobility resolution is the almost complete absence of diffusion broadening of the ion signals. Any diffusion before the barrier is reached has no effect, at least for the first method. For the second method, the brief time to cross the field barrier has the same effect. After crossing the barrier, when the ions are separated according to their mobility, diffusion may have a detrimental effect. The ions should therefore be brought to the ion detector or mass analyzer as quickly as possible to keep the diffusion small. On the way to the ion detector or mass spectrometer, the temperature of the adiabatically cooled gas jet is very low, however, which greatly reduces the diffusion in a favorable way.

The shape of the gas jet and speed of its molecules resulting from the free expansion of the gas from the aperture depend on the shape of the nozzle. In the publication by J. S. Page et al., a gas jet at the speed of sound is postulated for a simple cylindrical hole in a thin wall. If a sufficiently large pressure difference exists between the two sides of the aperture, a Laval nozzle can generate a supersonic jet traversing the vacuum chamber. This supersonic jet can then push the ions over the potential barrier. The formation of a gas jet with the speed of sound, or even a supersonic jet, shall explicitly be included here when free adiabatic expansion of the gas from an aperture into the surrounding vacuum is discussed.

The ion mobility spectra represent the distribution of the ions over different conformational or structural isomers. The structural isomers are usually very stable and therefore they are practically always measured strongly proportional to their concentrations in the sample. Conformational isomers, on the other hand, can transform into other forms at higher temperatures; their distribution in the ion mobility spectrum shows only how their original distribution in the sample was modified by processes in the ion source and in further steps by temperatures of surrounding gases. Such transitions can be avoided by carefully keeping the gas temperatures low; but they can also be deliberately brought about by changing the temperature of the gases surrounding the ions, and be investigated.

In some electrospray ion sources, for example, the temperature of the curtain gas can be varied between −70 and +300 degrees Celsius. A hot curtain gas is used if it is necessary to free the analyte ions from their solvate sheath. But there are many types of analyte molecule whose ions do not form a solvate sheath, or whose solvate sheaths disappear of their own accord in the vacuum. For these ions, the transitions between different conformational isomers can be investigated by careful temperature management. If the ions are produced in a very cold curtain gas, the original folding structure of the analyte molecules will be conserved to a large extent. The curtain gas becomes progressively colder when it is introduced into the vacuum system via the inlet capillary and on its subsequent passage through the mass spectrometer, and therefore cannot effect any changes to the folding structure. If the temperature of the curtain gas in the ion source is now increased either continuously or incrementally, newly appearing conformational isomers can be found by acquiring series of mobility spectra. Careful measurements of the gas temperatures in the ion source allow the heights of the energy barriers between the different conformational isomers to be measured.

If the ion source is operated continuously with cold curtain gas, the curtain gas can also be heated by suitable means at a different location, for example in the first ion funnel, and used for the investigation of conformational transitions. It is also possible to introduce temperature-controlled gas to the mass spectrometer at other locations and to use it for conformational studies.

DC field barriers with different shapes can be generated by individual apertures, and also by combinations of apertures. A known combination of apertures is the so-called "Einzel lens", which consists of three diaphragms with apertures the two outer ones being at the same potential. The height of the potential barrier can be adjusted by a voltage on the center diaphragm. The shape of the field maximum in front of the potential saddle can be readily shaped in Einzel lenses by selecting the spacing between the diaphragm apertures and their diameters.

Instead of a real DC field barrier to generate the field maximum, a barrier of a pseudopotential can be used, which can be generated preferably by an RF voltage at a bipolar grid across the jet; but also RF voltages at an aperture at the end of the ion funnel will generate such a barrier. The field maximum of the pseudopotential barrier sharpens the mobility selection because the maximum of the pseudofield allows not only ions below a mobility threshold, but also those above a mass threshold to pass. Pseudofields exert a pseudoforce on ions which is inversely proportional to their mass. A combination of pseudofields and real fields can also be used.

The ion guides required to canalize the ions to the potential barrier can have very different forms. They can be multipole rod systems, for example, which are operated with RF voltages, like that presented in FIG. 10. They can also be systems of parallel ring diaphragms or ion funnels, in which case radially focusing pseudopotentials can be mixed with DC voltage gradients that drive the ions forward in the axial direction to redirect them into the gas jet. However, the ion guide system can simply be an ion-optical lens system without applying RF voltages. It has long been known that an arrangement of parallel diaphragms with apertures to which alternating DC potentials are applied, acts as an ion guide which continuously focuses toward the axis if ions transit this arrangement with sufficient velocity, either by virtue of their own inertia or when driven by a gas. The potential barrier can then be generated by one of the apertures within the arrangement, or by a further aperture behind this arrangement.

In order to then increase (or decrease) the lateral guidance force of the ion guides when the opposing fields at the potential barrier change, the voltages at the ion guides can be changed in synchronization with the voltage of the potential barrier. Care must be taken here that the ion current is not changed so much by the change to the lower mass threshold of the ion guides that, after differentiation, false ion mobility signals are generated. This can particularly happen when there are stronger ion signals in the lower mass range which suddenly appear or disappear when the lower mass threshold is changed. Since the light ions of the lower mass range up to 500 daltons, for example, usually contribute nothing at all to the mobility spectrum, it is advantageous to filter out the light ions before they reach the potential barrier. In arrangements according to FIG. 1 or 2, which each have two ion funnels, this filtering out can be done in the first ion funnel, for example, by a potential barrier at the ring diaphragm (6), i.e. according to the method of J. S. Page et al.

Instead of increasing the RF voltages at the ion guides, the frequency of the RF voltage can be decreased. This measure also improves the guiding of heavier ions, as is known for pseudopotentials.

If the potential barrier in FIG. 2 is raised by increasing the voltage at the diaphragm aperture (9), the velocity of the ions, which they possess on entering the next ion guide system (11), can change. They can receive this velocity when rolling down from the potential barrier if the gas density is not high enough to reduce this velocity immediately back to the velocity of the gas by the damping action in the gas. Differing velocities can, however, change the acceptance of the ion guide (11) with respect to the ions entering, and thus change the ion current as a whole. Since the acceptance is mass-dependent, the ion current can even change as a function of the mass. In order to exclude such a change in the acceptance resulting from a changing potential difference between diaphragm (9) and ion guide (11), it is possible to jointly change all the voltages at the instrument parts (5), (6) and (8) in front of the ring diaphragm (9) instead of changing the voltage at the diaphragm (9). It is also possible to couple the changes to all voltages at the instrument parts behind the ring diaphragm (9) to the voltage at the ring diaphragm (9) itself.

The acquisition methods for mobility spectra can be calibrated by ions whose mobilities are known. The calibration function $K_0=f(V)$ as a function of the height V of the potential barrier turns out to be virtually linear over wide ranges. After calibrating an acquisition method, the mobility spectra can be converted from potential barrier coordinates V to mobility coordinates $K_0$. From these calibrated spectra, the values $K_0$ for the mobilities of the individual ion species and the mobility resolution $R_{mob}=K_0/\Delta K_0$ of the method can be determined.

For comparisons of measured mobilities with computed mobilities for different conformations of one ion species, it is advantageous to use monoatomic helium as the drift gas because the calculations become simpler. The helium can be used as the curtain gas in an electrospray ion source, passing together with ions through an inlet capillary and into the vacuum system, where the differential evacuation forms it into a jet of gas through the ion guides.

If no such comparison of measured and computed mobility values is planned, nitrogen, clean air or other gases can be used as the curtain gas in the electrospray ion source and for the formation of the jet of gas. For calibrations, in particular, it must be remembered that nitrogen and other gases produce mobility values which are different to those for helium. Another advantageous gas for mobility measurements is argon.

The gas, from which ultimately the gas jet according to the invention is formed, is in most cases added in the electrospray ion source as curtain gas. It accepts the ions and guides them through the inlet capillary into the first stage of the vacuum system. The curtain gas is usually heated to around 200 to 300 degrees Celsius in order to contribute to the desolvation of the ions in the capillary; the gas is greatly cooled in the inlet capillary itself, and particularly in the transitions of the differential pumping stages. It has also been elucidated, however, that the curtain gas can be greatly cooled, for example down to the temperature of liquid nitrogen, before being introduced into the inlet capillary. Cooled curtain gas can contribute to an increase in the mobility resolution of the method according to the invention. The temperature of the curtain gas can also be used to investigate temperature-dependent conformational changes of the ions as a result of changes to the folding, however.

The gases which form the gas jet by emerging from an aperture into the surrounding vacuum can also be added later, at a different location along the path of the ions from the ion source to the ion detector. Some mass spectrometers already have such gas feeds, which are used to fill collision cells for the fragmentation of ions. These collision cells generally take the form of ion guides, and can therefore be used according to the invention for mobility investigations.

For ion mobility measurements in long drift regions, a pressure range of a few hectopascals is usually selected. The acquisition times for a mobility spectrum then amount to a few hundred microseconds. However, according to the equation given above for the part of the mobility resolution determined by the diffusion, the mobility resolution does not depend at all on the pressure. One could therefore apply lower pressures without any disadvantage. But at lower pressures, the drift velocity is higher, which makes the acquisition time for a mobility spectrum so short that only very fast and expensive transient recorders can be used to measure the ion currents.

These considerations do not apply to mobility measurements with methods according to this invention. The mobility resolution seems rather to increase at lower pressures, possibly because the velocity of the adiabatically cooled gas jet is more homogeneous; or even as a result of the formation of a gas jet with the speed of sound. At the end of the second ion funnel (8) from FIG. 1, there is a pressure of between a few pascals and a few tens of pascals only. Methods according to the invention can therefore preferably be carried out at pressures below a few tens of pascals.

The advantage of the methods and instruments according to the invention is the combination of the relatively high mobility resolution and compact size of the necessary devices. A further advantage is that the necessary devices can easily be incorporated into a mass spectrometer. A number of mass spectrometers even already have the necessary devices in a readily usable form.

Persons skilled in the art can easily use this invention as the starting point to develop further application methods and further embodiments. These application methods and embodiments shall be included here in this patent protection application.

What is claimed is:

1. A method for sorting ions into a first group of ions that are pushed over an electric field barrier by a flow of a gas and a second group of ions that are held back by the electric field barrier, comprising:
    (a) forming the flow of the gas as a jet by adiabatic expansion of the gas through a nozzle.

2. The method of claim 1, wherein step (a) comprises adiabatically expanding the gas through a Laval nozzle.

3. The method of claim 1, wherein step (a) comprises locating the nozzle in a wall between two chambers of a differential pumping system.

4. The method of claim 1, further comprising (b) measuring the first group of ions without mass separation by an ion detector.

5. The method of claim 1, further comprising (b) measuring the first group of ions with mass separation by a mass analyzer.

6. A method for sorting ions, comprising:
    (a) entraining the ions in a flow of gas;
    (b) forming the flow of the gas into a jet by adiabatic expansion of the gas through a nozzle; and
    (c) placing an electric field barrier downstream in the flow of gas from the nozzle, the electric field barrier having a height so that the ions are sorted into a first group of ions that are pushed over an electric field barrier by the flow of a gas and a second group of ions that are held back by the electric field barrier.

7. The method of claim 6, wherein step (c) comprises generating the electric field barrier by DC potentials or RF pseudopotentials at one or more electrodes.

8. The method of claim 6, wherein the nozzle has an exit from which the jet issues and step (c) comprises locating the electric field barrier adjacent the nozzle exit.

9. The method of claim 6, wherein the nozzle has an exit from which the jet issues and step (c) comprises locating the electric field barrier at a predetermined distance from the nozzle exit and placing an ion guide around the jet between the nozzle exit and the electric field barrier so that ions are contained in, and redirected into the gas jet.

10. The method of claim 9, wherein step (c) comprises forming the ion guide as one of an RF multipole rod system, an RF ion funnel, and a system of parallel diaphragms with apertures, alternately connected to one of DC voltages of alternating polarity and two phases of an RF voltage.

11. The method of claim 10, wherein step (c) comprises forming the RF multipole rod system with sufficiently thin pole rods, and fitting the apertures of the diaphragms with skimmers, so that expanding gas outside the jet can escape without substantial hindrance.

12. The method of claim 10, wherein the electric field barrier height is variable and step (c) comprises varying at least one of the magnitude and frequency of the RF voltage at the ion guide as the height of the electric field barrier is varied.

13. The method of claim 9, further comprising:

(d) adjusting the height of the electric field barrier so that ions are collected in the ion guide;
(e) stopping generation of the ions;
(f) lowering the height of the electric field barrier; and
(g) measuring an ion current of ions pushed over the lowered electric field barrier by the gas jet to directly measure the ion mobility.

14. The method of claim 13, wherein step (g) comprises acquiring a series of mass spectra as the height of the field barrier is lowered in step (f), and extracting mobility spectra of ions of individual mass ranges without differentiation from the series of mass spectra.

15. The method of claim 14, further comprising:
(h) examining the mobility spectra extracted in step (g) to select ions with predetermined mobilities; and
(i) acquiring fragment ion spectra of the selected ions.

16. The method of claim 6, wherein step (a) comprises supplying a continuous current of ions from an ion source, and wherein the method further comprises:
(d) varying the height of the electric field barrier;
(e) measuring the ion current of the first group of ions as a function of the height of the field barrier; and
(f) differentiating the ion current with respect to the height of the field barrier to generate a mobility spectrum.

17. The method of claim 16, wherein step (e) comprises acquiring a series of mass spectra and extracting ion current curves for ions of individual mass ranges from the mass spectra, and wherein step (f) comprises differentiating the ion current curves to generate mobility spectra.

18. The method of claim 16, wherein the gas in which the ions are entrained has a temperature and wherein the method further comprises:
(g) changing the temperature; and
(h) acquiring mobility spectra at various gas temperatures to determine conformational changes of the ions.

19. An ion mobility spectrometer, comprising:
an ion source that entrains ions in a gas flow;
a differential pumping system, transporting the gas flow and ions through a plurality of sequential pumping chambers;
a nozzle having an exit and being located in a wall between two of the pumping chambers, so that the gas flow passes through the nozzle and generates a gas jet with ions at the nozzle exit;
a device for generating adjacent to the nozzle exit an electric field barrier having an adjustable height; and
an ion detector that measures a current of ions that are pushed over the electric field barrier by the gas jet.

20. An ion mobility spectrometer, comprising:
an ion source that entrains ions in a gas flow;
a differential pumping system, transporting the gas flow and ions through a plurality of sequential pumping chambers;
a nozzle having an exit and being located in a wall between two of the pumping chambers, so that the gas flow passes through the nozzle and generates a gas jet with ions at the nozzle exit;
an ion guide having an entrance located at the nozzle exit and an exit, the ion guide maintaining and redirecting ions into the gas jet;
a device for generating adjacent to the ion guide exit an electric field barrier having an adjustable height; and
an ion detector that measures a current of ions that are pushed over the electric field barrier by the gas jet.

21. The ion mobility spectrometer of claim 20, wherein the ion detector comprises a mass spectrometer.

* * * * *